United States Patent
He et al.

[11] Patent Number: 6,163,592
[45] Date of Patent: Dec. 19, 2000

[54] BEAM SCATTERING MEASUREMENT SYSTEM WITH TRANSMITTED BEAM ENERGY DETECTION

[75] Inventors: Bob Baoping He; Kingsley L. Smith, both of Madison, Wis.

[73] Assignee: Bruker AXS, Inc., Madison, Wis.

[21] Appl. No.: 09/239,419

[22] Filed: Jan. 28, 1999

[51] Int. Cl.[7] .................................................. G01N 23/20
[52] U.S. Cl. ................................. 378/71; 378/70; 378/73
[58] Field of Search ................................. 378/70, 71, 73, 378/75, 156

[56] References Cited

U.S. PATENT DOCUMENTS

| | | | |
|---|---|---|---|
| 5,491,738 | 2/1996 | Blake et al. | 378/71 |
| 5,589,690 | 12/1996 | Siewert et al. | 250/390.06 |
| 6,005,913 | 12/1999 | Zombo et al. | 378/71 |

OTHER PUBLICATIONS

Chess Newsletter 1995, pp. 48–50, 52.
B. D. Cullity. Elements of X–Ray Diffraction, Second Edition (Reading, MA: Addison–Wesley, 1978), pp. 92, 93, 150–156.
Dr. John D. Barnes; SAXS From Polymers; APS–DHPP Short Course, Mar. 19, 1994; National Institute of Standards and Technology, Gaithersburg, MD 20899 USA; pp. 1–27, 73, 143.

*Primary Examiner*—David P. Porta
*Assistant Examiner*—Allen C. Ho
*Attorney, Agent, or Firm*—Kudirka & Jobse, LLP

[57] ABSTRACT

A radiation scattering measurement system, such as an x-ray diffraction system, uses a modified beamstop, or attenuator, to allow simultaneous detection of energy scattered from a sample and energy transmitted through the sample. Rather than entirely blocking the transmitted beam energy from reaching a detector of the system, the attenuator blocks only an outer portion of the transmitted beam, so that a shadow region is created on the detector surrounding the detector region upon which the transmitted beam is incident. This local region of minimum intensity defines a boundary on the detector between the transmitted beam energy and the energy scattered from the sample. The attenuator also reduces the per-unit-area intensity of the transmitted beam using a broadband filter element, so that the transmitted beam does not saturate the detector. A single detector frame is taken containing the beam energy and the scattered energy, and the minimum intensity boundary between the two is located. The measurements from the different detector regions are then used to determine the relative intensity between the transmitted beam and the scattered energy, and a transmission coefficient is calculated.

30 Claims, 4 Drawing Sheets

BEAM SCATTERING MEASUREMENT SYSTEM WITH TRANSMITTED BEAM ENERGY DETECTION

FIELD OF THE INVENTION

The invention relates generally to the field of electromagnetic signal and high-energy particle detection and, more particularly, to the accurate measurement of diffraction patterns in scattering detection apparatus.

BACKGROUND OF THE INVENTION

Measurement systems such as x-ray diffraction devices, neutron diffraction devices or similar diffraction devices that use other radiation sources, rely on a diffraction pattern from the radiation scattered by a sample to make a desired measurement. An x-ray diffraction system operating in this manner is depicted in schematic form in FIG. 1. As shown, the system is arranged for transmission mode diffraction. An x-ray radiation source 10 directs a beam of x-rays 12 onto a specimen 14 to be examined. The x-rays are scattered from the specimen in a pattern indicative of its atomic structure. This scattered energy may thereafter be detected by a two-dimensional (2D) detector 18, which detects the transmission variation of the scattered signal in the plane perpendicular to the direction of the original beam.

As in most transmission mode diffraction systems using 2D detectors, this system uses a beamstop 20 to block the direct x-ray beam that passes through the sample from reaching the detector. This prevents the detection of the diffracted energy from being disturbed by interaction of the high-energy transmitted x-ray beam with the detector. However, in certain circumstances, it is desirable to measure the intensity of the transmitted beam to allow normalization of the diffraction data against the sample thickness (or density) variation. The conventional manner of doing so is shown in FIG. 1. A glassy-carbon (GC) filter 16, which has high-angle scattering that is featureless, is inserted in the path of the transmitted x-ray beam, and the resulting two-dimensional pattern is detected. From this, the desired information regarding the intensity of the transmitted beam may be determined.

While the use of a GC filter has proven a satisfactory way of detecting the transmitted beam intensity, it requires the insertion and removal of the filter. Furthermore, a separate detection step must be performed for each of the transmitted beam and the actual diffracted x-ray energy. This creates delays and additional steps in the ultimate x-ray diffraction measurement process.

SUMMARY OF THE INVENTION

In accordance with the present invention, a radiation diffraction measurement system is provided that measures radiant energy diffracted from a sample. The system includes a radiant energy source from which a beam of radiant energy is directed. In the preferred embodiment, the radiant energy source is an x-ray source, but the invention may be equally applied to systems using other types of sources. A detector is also provided that detects the intensity of radiant energy incident upon different regions of it. This detected energy may include energy diffracted from the sample as well as energy received from the transmitted radiant energy beam. In particular, when the beam is directed at the sample being examined, some of the beam energy is diffracted, while some of is transmitted through the sample. The detector of the present invention detects both the diffracted energy and the transmitted beam energy, and does so simultaneously.

The beam transmitted through the sample is preferably attenuated to reduce its intensity magnitude prior to its reaching the detector. This allows a beam to be used that has sufficiently high energy to provide good energy diffraction from the sample, while preventing the high energy of the transmitted beam from saturating the detector. In a preferred embodiment, the attenuator will block an outer portion of the transmitted beam from reaching the detector. In this way, the attenuator creates a local minimum intensity region on the detection surface that surrounds the region of the detector upon which the beam is incident. This local intensity region is an easily detectable boundary between a region of the detector upon which the beam is incident and one upon which the diffracted energy from the sample is incident. Thus, a single detection frame of the detector will simultaneously contain intensity information on both the beam and the diffracted radiation. In the preferred embodiment, the attenuator also provides a filtering mechanism that provides a broadband reduction in the per-unit-area intensity of the beam.

The detector used with the system must be able to detect radiation intensity in different regions of the detection area. This allows detection of the beam intensity and detection of the diffracted energy to be done simultaneously. Preferably, the detector is a multi-element detector, and has a plurality of detection "pixels" across a detection surface, each of which generates an individual intensity measurement. When the beam is directed at the sample, a single detection "frame" is generated. Preferably, this frame is stored in a local data storage device. Thereafter, the regions of the detector upon which the transmitted beam and diffracted energy are incident, respectively, may be determined.

A preferred method of determining the relative intensities of the transmitted beam and the diffracted beam energy involves first transmitting the beam through the attenuator toward the detector without the sample in place. This "air scatter" provides a baseline, and may be used to determine the center of the region on the detector upon which the transmitted beam is incident. The resulting detector intensity frame from the air scatter is stored. A sample is thereafter loaded into the system, and a scan is initiated by directing the initial beam at the sample with the detector in an active state. A single frame from the detector is stored, and may then be analyzed to determine the region of the detector upon which the transmitted beam is incident.

With the beam center on the detector being known, intensity measurements from the frame are examined to locate local minimum intensity points surrounding the center. In a preferred embodiment, multiple radial directions from the center are examined until a local minimum is reached along each of the directions. These directions may be mutually orthogonal so as to determine the change in intensity in the frame in four primary directions from the center. The minimum intensity points closest to the center along these directions will lie in the shadow region created by the attenuator blocking the outer portion of the transmitted beam. From these points, interpolation may be used to determine a boundary surrounding the region of the detector upon which the transmitted beam is incident.

Once the beam region boundary on the detector is determined, the intensities measured within that region on the detector are integrated over the region itself to determine an average transmitted beam intensity. In a preferred embodiment, the measurements within the beam region from the air scatter may also used in the integration of the beam intensity along with those resulting from the transmitted beam during the sample measurement. The intensity values collected by the detector outside of the beam boundary during the sample measurement are then integrated over the area outside of the beam boundary to determine the average intensity of the diffracted radiation. Once the intensity calculations are made, a transmission coefficient may be calculated.

DETAILED DESCRIPTION OF THE PREFERRED EMBODIMENT

Figure 1:
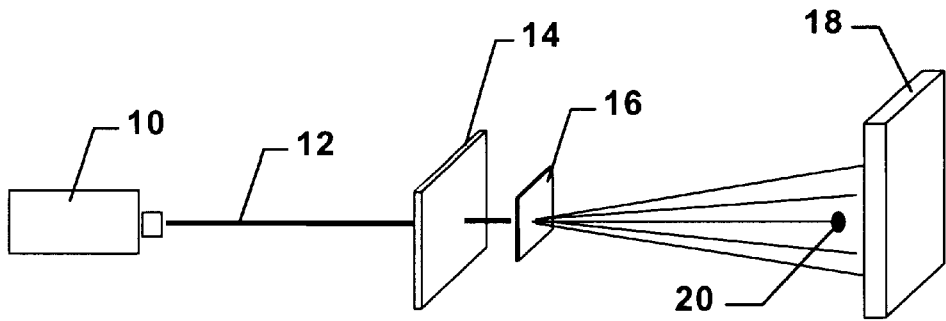
FIG. 1 is a diagrammatic view of a radiant energy diffraction measurement system according to the prior art.
Figure 2:
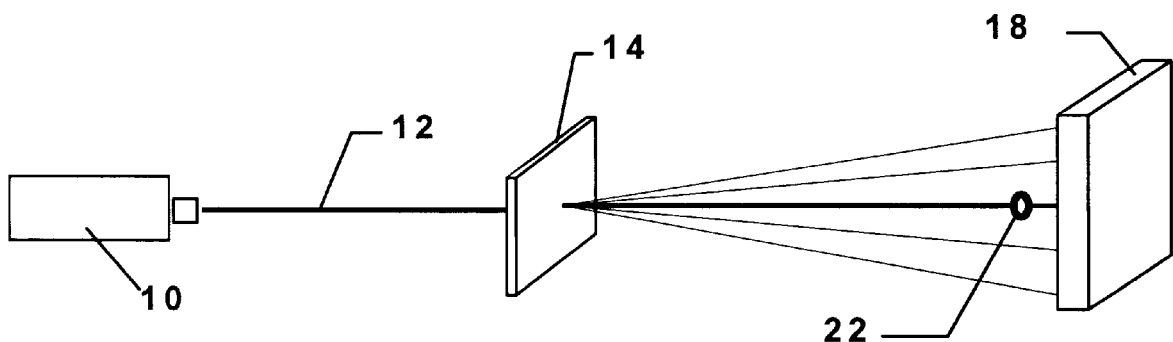
FIG. 2 is a diagrammatic view of a radiant energy diffraction measurement system according to the present invention.

Shown in FIG. 2 is an x-ray diffraction apparatus according to the present invention. An x-ray radiation source 10 directs an x-ray beam 12 at a sample 14 under test. As is known in the art, the interaction of the x-ray beam with the molecular structure of the sample causes diffraction of the x-rays such that a diffraction pattern is produced. This diffraction pattern is detected by 2D detector 18, and the pattern indicates the nature of the interaction with the sample 14, and therefore provides information about its molecular structure.

Also shown in FIG. 2 is a beamstop 22 according to the present invention. As in prior art beamstops, beamstop 22 is located in the path of the portion of the x-ray beam that is transmitted through the sample 14. However, beamstop 22 does not simply block the x-ray beam from reaching the detector. Instead, the beamstop 22 functions as an attenuator of the beam, allowing a center portion of it to reach the 2D detector 18. That is, an outer portion of the beam is completely blocked by the beamstop, but a center portion is allowed to pass through the beamstop, subject to a certain degree of additional attenuation. Hereinafter, the term "beamstop" will therefore be used interchangeably with the term "attenuator" in describing element 22 of the figures. The beamstop 22 is shown in more detail in FIG. 3.

Figure 3:
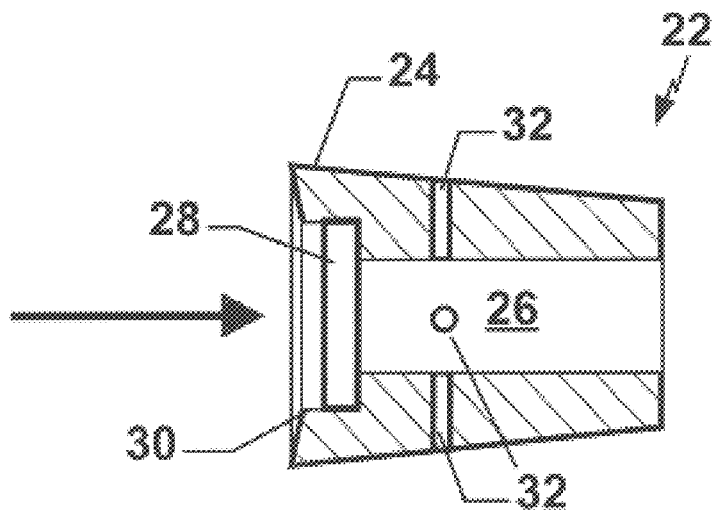
FIG. 3 is a cross sectional view of a radiant energy beam attenuator according to the present invention.

The cross section of FIG. 3 depicts a preferred embodiment of beamstop 22, with the arrow indicating the direction of the incident beam. As shown, housing 24 surrounds a center bore 26 through the beamstop. The bore 26 is preferably cylindrical, but may be other shapes as well, provided the shape is taken into account in the ultimate distribution of the energy transmitted through the beamstop. Those skilled in the art will recognize that FIG. 3 is not necessarily to scale and the diameter of the bore 26 and the diameter of the beamstop 22 are determined by the desirable beam size, beam divergence, sample-to-detector distance and other configuration parameters. The actual beamstop diameter is larger than the primary beam spot on the detector. For example, with a beam collimating pinhole having a diameter of 0.2 mm, the beam spot on a detector positioned 600 mm from the sample may be 2.5 mm given a particular beam divergence. A beamstop according to the present invention that would be appropriate for this configuration is 4 mm in diameter and has a bore 26 with a diameter of 1 mm. In such a case, approximately 84% of the crossing area of the beam spot is blocked by the beamstop 22. Due to the uneven distribution of the beam intensity profile, the portion of the beam not directly blocked by the beamstop 22 normally has a higher intensity per unit area. This portion of the energy is passed, but is subject to attenuation in the process.

Attenuation of the unblocked energy is provided by filter element 28, which resides in a front mounting region 30 of housing 24, which has a bore diameter greater than that of main bore 26. Thus, attenuation of the beam is provided both by the direct blocking of a portion of the beam by the beamstop, as well as by the filtering provided by the filter element. The filter element is preferably cylindrical, and may be constructed from any of a number of materials including copper, nickel, gold, aluminum, or any other homogenous material that will attenuate the beam without generating strong fluorescence. With such a material, the degree of attenuation may be controlled by controlling the thickness of the material. In the preferred embodiment of the invention, the filter causes a broadband reduction in the intensity of the transmitted beam. However, it is most important to attenuate in the wavelengths in the primary detection range of the detector 18. Naturally, the degree of attenuation may be controlled by other system parameters as well, such as the diameter of bore 26 and the intensity of the initial x-ray beam. In a preferred embodiment, the bore 26 has a diameter of 1 mm, and the filter element 28 is made of nickel and has a thickness of 0.1 mm. These specifications are effective, for example, when used with a "HI-STAR" area detector, manufactured by Bruker Analytical X-Ray Systems, Inc., Madison, Wis., and an expected transmitted x-ray beam intensity of 10–100 counts/second/pixel.

The beamstop of FIG. 3 also includes mounting bores 32 in two perpendicular directions. These bores allow the attachment of wires to the beamstop to allow it to be precisely positioned. The wires are held tight in four directions to a linear adjustment mechanism so that the beamstop position can be adjusted. The linear adjustment may also be done through motion feedthroughs so the beamstop can be kept in a vacuum or other isolated environment. Those skilled in the art will recognize that other positioning mechanisms may be substituted as well without deviating from the principles of the invention.

After attenuation by beamstop 22, the transmitted beam is incident upon detector 18 (FIG. 2). In its attenuated form, it does not saturate the detector, and its intensity can be effectively quantified. By blocking a portion of the beam that surrounds the center portion, a shadow region is produced at the detector that separates the detected transmitted beam from the detected scattered x-rays. This shadow region allows the detected transmitted beam to be accurately distinguished from the detected scattered x-ray pattern. Thus, the detected intensity of the transmitted x-ray beam can be determined, and used to normalize the detected signal of the scattered x-rays.

Figure 4:
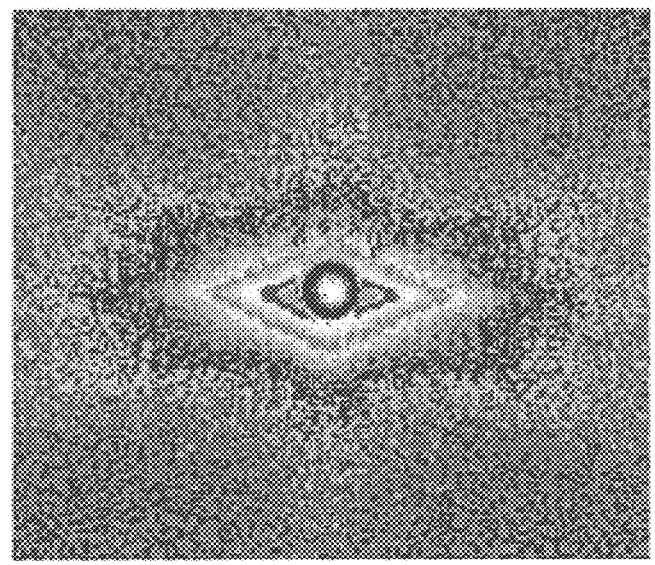
FIG. 4 is a still image resulting from a measurement using the measurement device of the present invention.

A still image of the signal detected by detector 18 during an experiment using the present invention is shown in FIG. 4. As shown, a bright spot is present at the center of the image, indicating the location at which the transmitted and attenuated x-ray beam was incident on the detector. Surrounding the bright spot is a ring of shadow, where the beamstop blocked any x-ray energy of the transmitted beam from reaching the detector. This shadow region separates the bright spot of the transmitted beam from the remainder of the diffracted x-ray energy, which forms the pattern that surrounds the shadow region of the image in FIG. 4.

To properly adapt the present invention to modern processing equipment, software used with the detector is modified to allow simultaneous processing of the spot from the transmitted beam and the diffraction pattern surrounding it. The general steps for doing this processing are shown in flowchart form in FIGS. 5A and 5B. The software instructions to implement these steps are located in a storage medium local to the scanning apparatus. The specific instructions themselves may vary depending on the equipment being used, and the creation of a program having these instructions is well within the ability of those skilled in the art given the description herein.

Figure 5A:
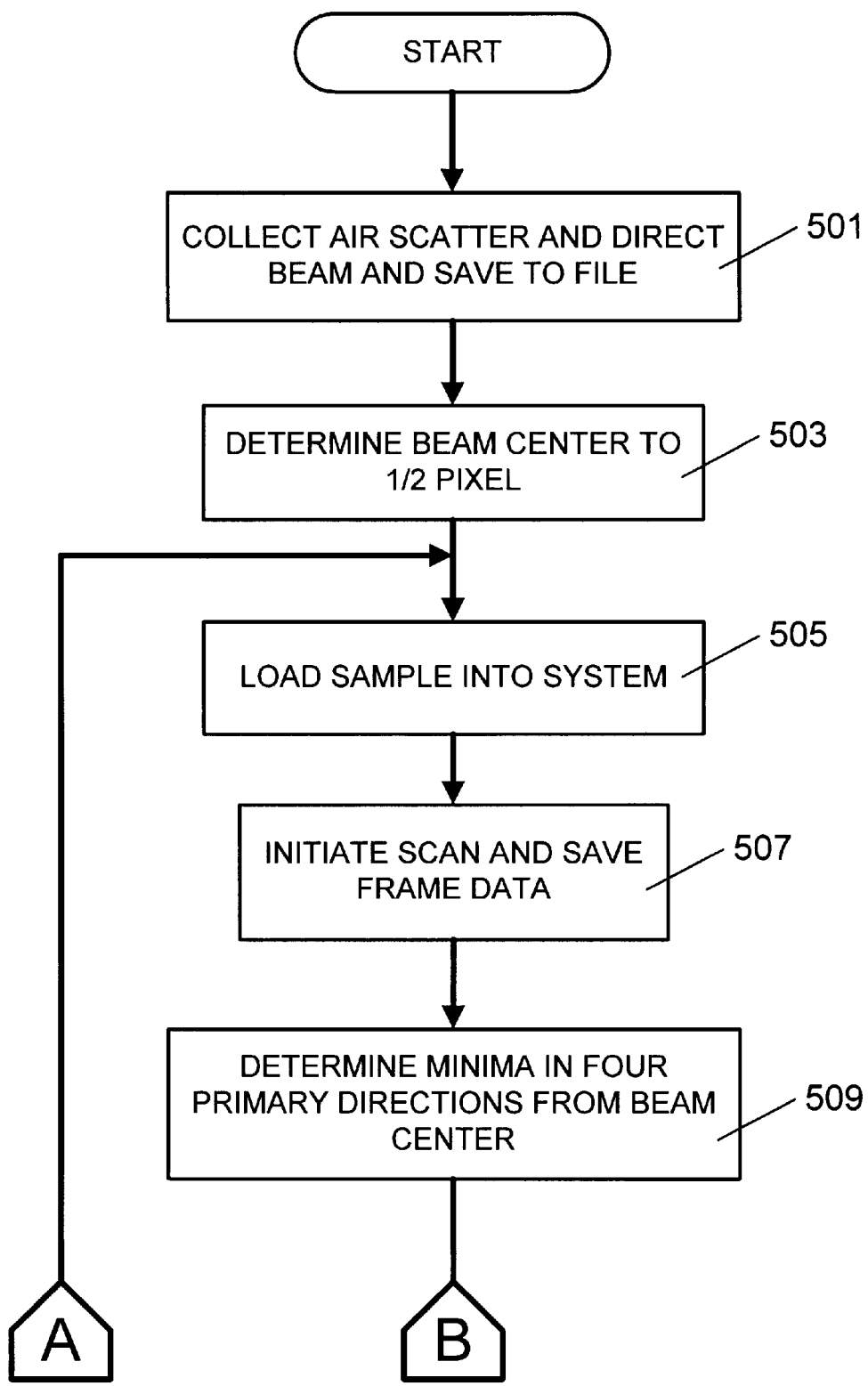
FIGS. 5A and 5B, taken together, form a flowchart generally depicting a set of steps performed while using a measurement device according to the present invention.

FIG. 5A shows a first portion of a processing procedure according to the present invention. In step 501, an x-ray diffraction scan is initiated with no sample in place, that is, an "air" scattering is done. The signal levels detected by the detector array during the air scatter are stored as a single file. From this detected signal, the approximate location of the center of the transmitted beam is also determined (step 503). Since the beamstop causes a shadow to be formed around the transmitted beam portion, the portion of the detector array upon which the beam is incident may be easily detected. In practice, the beam location is has been found to be detectable to within one-half pixel on the detector array. With the beam center having been located, a sample is then loaded into the system (step 505). In step 507, an x-ray diffraction scan of the sample is performed, and the intensities detected by the detector are recorded in a detection file. From this detection file, analysis of the scan data may be performed.

With the data having been collected, the extent of the transmitted beam region is determined. First, four primary directions from the beam center are selected, and a minimum detected intensity level is found along each direction (step 509). That is, four mutually orthogonal axes that radiate out from the previously determined beam center on the detector are selected, and the intensity values are examined along each of these axes until a minimum value is reached. Since the minima should fall within the shadow region surrounding the transmitted beam, the determined minima may be used as points that define the limits of the transmitted beam in four directions on the surface of the detector. The boundary defined by the shadow region is then interpolated from the four minimum intensity points and knowledge of the beam characteristics. For example, the beam shape in the system of FIG. 2 is elliptical, so an ellipse is interpolated from the detected minima. This ellipse is then used to define the region of the transmitted beam incidence on the detector (step 511).

With the regions of the detector surface defined, scan measurements are then made. In step 513, the scan intensity outside of the ellipse is integrated, giving the signal intensity of the scattered x-rays. The scan intensity within the ellipse is also integrated to determine the intensity of the transmitted beam (step 515). To improve the quality of the transmitted beam measurement, the integration of beam intensity in the preferred embodiment of the invention uses both the beam intensity measured during the scattering measurement of step 507 and the beam intensity measured during the test measurement of step 501. Alternatively, the integration may use just the beam measurement made during the scattering. Although some of the scattered x-rays may be scattered into the elliptical region defining the transmitted beam, the intensity of the transmitted beam is several orders of magnitude greater than that of the scattered x-rays, and the effect is therefore negligible.

Following the intensity measurements, a transmission coefficient may be calculated, as shown in step 517. The transmission coefficient is the ratio of the test beam intensity from step 501 to the transmission intensity from step 515. Once this coefficient has been determined, it may be used to calculate the sample density or thickness at the particular sample position.

Figure 5B:
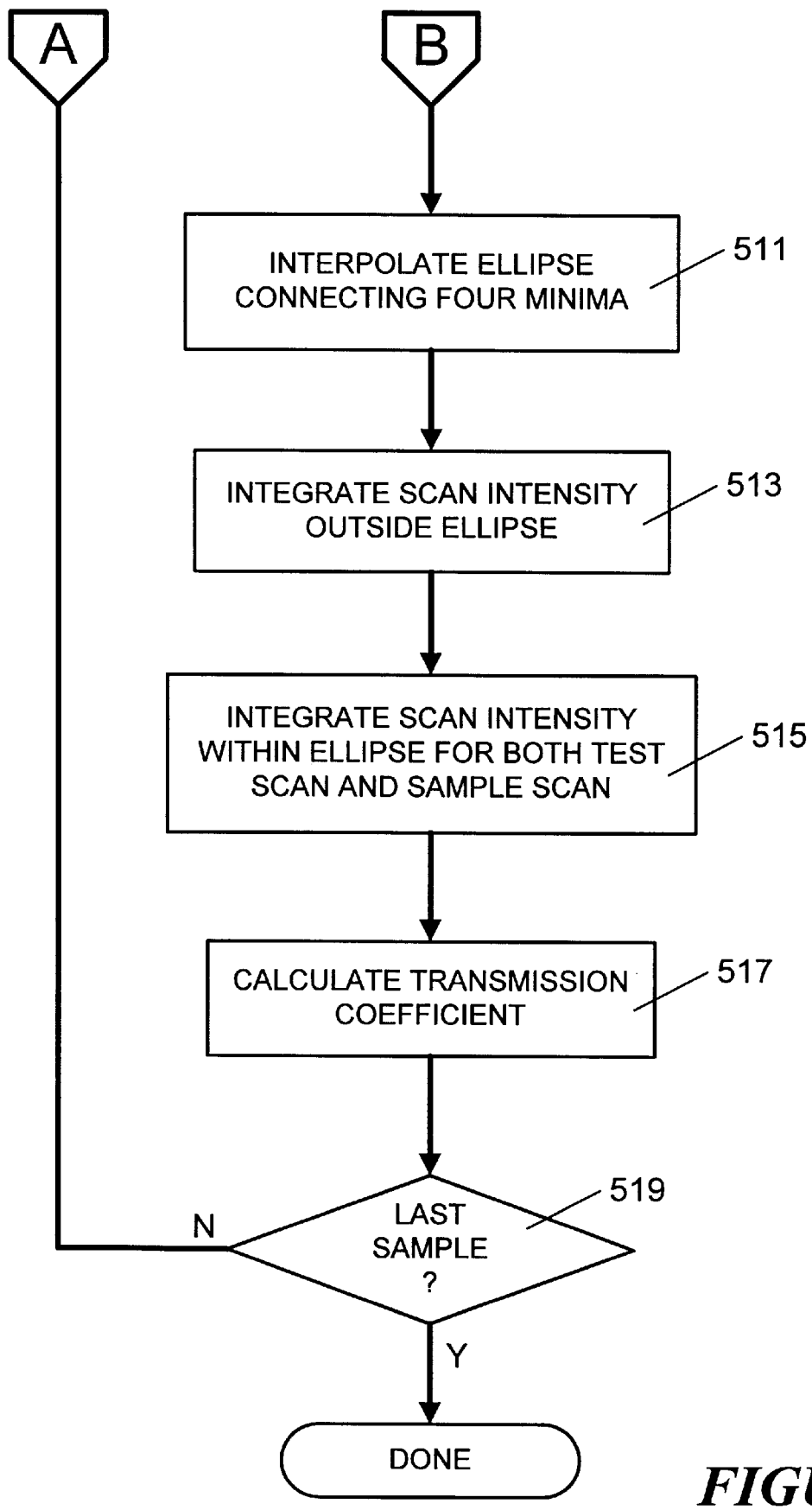

Step 519 of FIG. 5B shows a return to step 505 to load another sample if desired. Since the initial air scattering serves as a calibration of the system, it is not necessary to perform this step again before beginning another scan. Once the last sample has been examined, the procedure is terminated. Preferably, the calibration steps are repeated for each new set of scattering measurements. It will be apparent to those skilled in the art that, although the steps of calculating intensities and the transmission coefficient are shown prior to the loading of a new sample, the measurements may also be stored and the calculations done later. The calculations may also take place while subsequent samples are being examined.

While the invention has been shown and described with reference to a preferred embodiment thereof, it will be recognized by those skilled in the art that various changes in form and detail may be made herein without departing from the spirit and scope of the invention as defined by the appended claims.

What is claimed is:

1. A radiation diffraction measurement system that measures radiant energy diffracted from a sample, the system comprising:
    a radiant energy source from which a beam of radiant energy is directed to the sample;
    a detector that detects the intensity of radiant energy incident upon different regions of the detector, including energy diffracted from the sample; and
    an attenuator that attenuates a transmitted beam of radiant energy that passes through the sample, such that a portion of the transmitted beam is incident on the detector while a portion of the beam is blocked by the attenuator from reaching the detector.

2. A measurement system according to claim 1 wherein the radiant energy source is an x-ray source.

3. A measurement system according to claim 1 wherein the detector comprises an array of detection pixels each of which generates an individual intensity measurement.

4. A measurement system according to claim 1 wherein the detector simultaneously detects the attenuated beam and the energy diffracted from the sample.

5. A measurement system according to claim 1 further comprising a data storage device in which the intensities detected by the detector are stored.

6. A measurement system according to claim 1 wherein the attenuator blocks an outer portion of the transmitted beam such that it does not reach the detector.

7. A measurement system according to claim 6 wherein diffracted energy from the sample is incident upon a first region of the detector that is adjacent to a second region of the detector upon which the transmitted beam is incident, and wherein blocking of the transmitted beam by the attenuator is such that a local minimum intensity region is created between the first detector region and the second detector region.

8. A measurement system according to claim 1 wherein the attenuator reduces the intensity of the transmitted beam per unit area.

9. A radiation diffraction measurement system that measures radiant energy diffracted from a sample, the system comprising:
- a radiant energy source from which a beam of radiant energy is directed to the sample;
- a detector that simultaneously detects the intensity of radiant energy diffracted from the sample in a first detector region and a beam of radiant energy that is transmitted through the sample in a second detector region; and
- an attenuator that attenuates the beam of radiant energy that is transmitted through the sample such that an outer portion of the transmitted beam does not reach the detector and an inner portion of the transmitted beam is incident on the detector, the attenuation creating a local minimum intensity region between the first detector region and the second detector region.

10. A method of measuring radiant energy diffracted from a sample, the method comprising:
- directing a beam of radiant energy toward the sample such that radiant energy is diffracted by the sample and a beam of radiant energy is transmitted through the sample;
- attenuating the beam of radiant energy transmitted through the sample prior to its reaching the detector such that a portion of the transmitted beam is incident on the detector while a portion of the beam is blocked by the attenuator from reaching the detector; and
- detecting, with a detector, the intensity of radiant energy incident upon different regions of the detector, including energy diffracted from the sample and the beam of radiant energy attenuated by the attenuator.

11. A method according to claim 10 wherein directing a beam of radiant energy toward the sample comprises directing an x-ray beam toward the sample.

12. A method according to claim 10 wherein detecting with the detector comprises detecting the radiant energy intensity with a detector comprising an array of detection pixels each of which generates an individual intensity measurement.

13. A method according to claim 10 wherein detecting with the detector comprises simultaneously detecting the attenuated beam and the energy diffracted from the sample.

14. A method according to claim 10 further comprising storing the detected intensities together in a data storage device as a single detection frame.

15. A method according to claim 10 wherein attenuating the beam of radiant energy comprises blocking an outer portion of the transmitted beam such that it does not reach the detector.

16. A method according to claim 15 wherein blocking an outer portion of the transmitted beam comprises blocking an outer portion of the transmitted beam such that a local minimum intensity region is created between the first detector region and the second detector region.

17. A method according to claim 10 wherein attenuating the beam of radiant energy comprises reducing the intensity of the transmitted beam per unit area.

18. A method according to claim 10 further comprising, in addition to directing the beam of radiant energy toward the sample, directing the beam toward the detector, attenuating the beam and measuring the intensity of the beam with the detector and without the sample in place, the intensity measurement made without the sample in place being used in conjunction with the detected radiant intensity of the beam that passes through the sample in determining an intensity measurement of the beam.

19. A method according to claim 10 wherein detecting the intensity of radiant energy transmitted through the sample comprises defining a region of the detector upon which the beam is incident, and integrating the detected intensity over that region.

20. A method according to claim 19 wherein defining a region of the detector upon which the beam is incident comprises determining an approximate point on the detector at which a center of the beam will be incident, detecting a plurality of minimum intensity points on the detector surrounding the center point, and establishing a beam boundary on the detector that contains the minimum detected intensity points.

21. A method according to claim 20 wherein establishing a beam boundary on the detector comprises interpolating a beam boundary using the minimum intensity points and a predetermined beam shape.

22. A method according to claim 21 wherein the predetermined beam shape is substantially elliptical.

23. A method according to claim 20 wherein detecting the intensity of radiant energy diffracted from the sample comprises integrating the intensity measured by the detector outside of the beam boundary over the detection area.

24. A method of measuring radiant energy diffracted from a sample, the method comprising:
- directing a beam of radiant energy toward a radiant energy detector, attenuating the beam and making a first measurement of the intensity of the attenuated beam with the detector;
- locating the sample in the path of the unattenuated beam and directing the beam toward the sample such that radiant energy is diffracted by the sample and a beam of radiant energy is transmitted through the sample;
- attenuating the beam of radiant energy transmitted through the sample prior to its reaching the detector;
- detecting, with a detector, the intensity of radiant energy incident upon different regions of the detector, including energy diffracted from the sample and the beam of radiant energy transmitted through the sample;
- determining a beam region of the detector upon which the transmitted beam is incident, and integrating the intensity detected in the beam region over that region as part of determining the beam intensity; and
- integrating the intensity measured by the detector in a region outside of the beam region over the outside region as part of determining the diffracted energy intensity.

25. A method according to claim 24 wherein integrating the intensity in the beam region comprises integrating the unattenuated intensity measurement of the beam over the beam region.

26. A method according to claim 24 wherein detecting energy diffracted from the sample and energy from the beam of radiant energy attenuated by the attenuator comprises detecting energy diffracted from the sample and energy from the beam of radiant energy attenuated by the attenuator simultaneously.

27. An attenuator for use in a radiation scattering measurement system having a radiant energy source that generates a beam of radiant energy that is incident upon a sample under test such that a portion of the beam is transmitted through the sample and a portion of the beam is scattered by the sample, and a detector that separately detects radiant energy, including the scattered energy and the transmitted beam energy, in different detection regions, the attenuator comprising:

a beam obstruction portion upon which a portion of the transmitted beam is incident prior to reaching the detector, the beam obstruction portion blocking a portion of the transmitted beam while allowing a different portion of the beam to reach the detector so as to create a region of reduced intensity on the surface of the detector that separates a portion of the detector upon which the transmitted beam is incident and a portion of the detector upon which the scattered energy is incident.

28. An attenuator according to claim 27 wherein the attenuator is a closed loop shape that blocks an outer portion of the transmitted beam.

29. An attenuator according to claim 27 further comprising a filter element that reduces the intensity of the transmitted beam per unit area.

30. An attenuator according to claim 27 further comprising mounting elements by which adjustments of the attenuator position may be made.

* * * * *